(12) United States Patent  
Jameson

(10) Patent No.: US 10,801,946 B2  
(45) Date of Patent: *Oct. 13, 2020

(54) ELECTRONIC MONITORING OF GAS ADSORBENT MEDIA BED

(71) Applicant: Pure Air Filtration, LLC, Norcross, GA (US)

(72) Inventor: Kevin F. Jameson, Norcross, GA (US)

(73) Assignee: Pure Air Filtration, LLC, Norcross, GA (US)

( * ) Notice: Subject to any disclaimer, the term of this patent is extended or adjusted under 35 U.S.C. 154(b) by 150 days.

This patent is subject to a terminal disclaimer.

(21) Appl. No.: 16/188,548

(22) Filed: Nov. 13, 2018

(65) Prior Publication Data

US 2019/0078998 A1 Mar. 14, 2019

Related U.S. Application Data

(62) Division of application No. 14/503,489, filed on Oct. 1, 2014, now Pat. No. 10,132,740.

(60) Provisional application No. 61/886,781, filed on Oct. 4, 2013.

(51) Int. Cl.
| | |
|---|---|
| G01N 17/04 | (2006.01) |
| G01N 27/12 | (2006.01) |
| G01N 33/00 | (2006.01) |
| B01D 53/04 | (2006.01) |
| B01D 53/30 | (2006.01) |

(52) U.S. Cl.
CPC ......... *G01N 17/04* (2013.01); *G01N 33/0031* (2013.01); *B01D 53/0454* (2013.01); *B01D 53/30* (2013.01); *G01N 27/122* (2013.01); *Y10T 29/49002* (2015.01)

(58) Field of Classification Search
CPC ...................... B01D 53/0423; B01D 53/0454; B01D 53/30; G01N 17/04; G01N 27/122; G01N 33/0031; Y10T 29/49002
See application file for complete search history.

(56) References Cited

U.S. PATENT DOCUMENTS

| | | | |
|---|---|---|---|
| 5,286,357 A | 2/1994 | Smart | |
| 10,132,740 B2* | 11/2018 | Jameson | ................ G01N 17/04 |
| 2006/0162431 A1 | 7/2006 | Harris | |
| 2012/0111190 A1 | 5/2012 | Dariavach | |

* cited by examiner

*Primary Examiner* — Lyle Alexander  
*Assistant Examiner* — Bryan Kilpatrick  
(74) *Attorney, Agent, or Firm* — Thomas Horstemeyer, LLP

(57) ABSTRACT

A method for manufacturing a device for electronically monitoring the consumption of gas adsorbent media in a media bed includes forming a monitoring rod of a corrosion resistant material. A plurality of sensors are attached to an exterior surface of the monitoring rod, and a communication channel is routed between each sensor and the connecting rod.

20 Claims, 7 Drawing Sheets

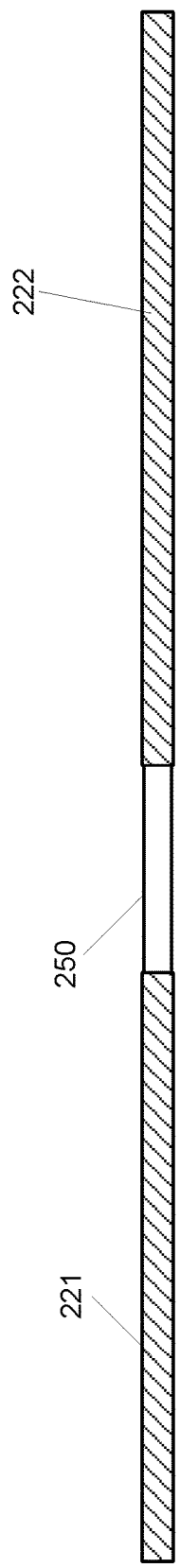
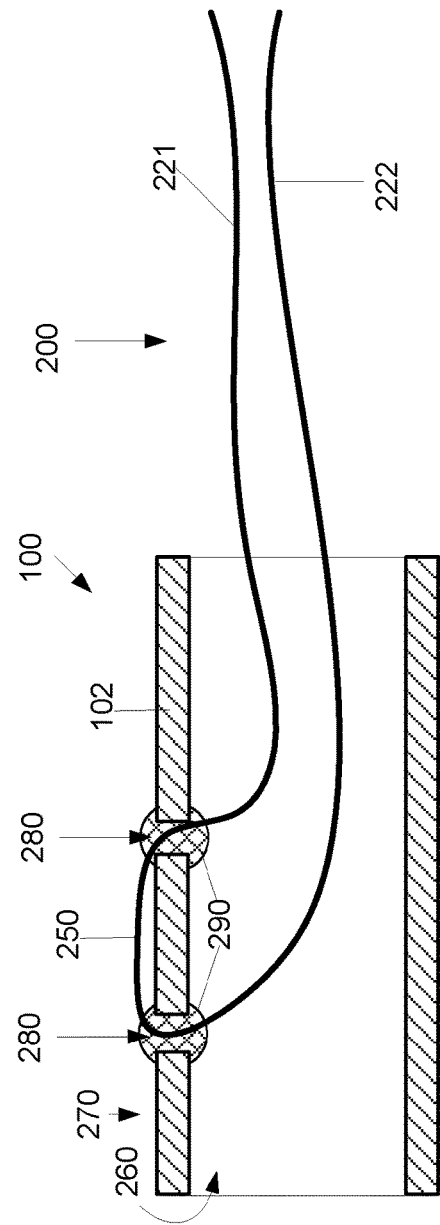

ELECTRONIC MONITORING OF GAS ADSORBENT MEDIA BED

CROSS-REFERENCE TO RELATED APPLICATIONS

This application is a divisional of U.S. patent application Ser. No. 14/503,489, filed Oct. 1, 2014, entitled "Media Bed Monitoring Device and System", which claims the benefit of U.S. Provisional Patent Application Ser. No. 61/886,781, filed Oct. 4, 2013, entitled "Media Bed Monitoring Device and System," both of which are incorporated by reference herein in their entireties.

FIELD OF THE INVENTION

The present invention is generally related to air purification systems, and more particularly is related to adsorbent media monitoring devices for air-purifying systems.

BACKGROUND OF THE INVENTION

Air purification systems remove harmful particulates and/or gasses from the air. In air purification systems, the use of loose granular media as an air purification adsorbent is limited by the ability to monitor the remaining longevity of the adsorbent media in use. When air purification systems that use gas adsorbent media are in use, air is drawn through adsorbent where the odorous or harmful gasses in the air are adsorbed. As the chemicals are adsorbed, they are captured inside the adsorbent media. However, as the media adsorbs more and more chemicals, the media becomes depleted and therefore needs to be changed out in order for the air purification system to continue to be effective.

The adsorbent media in the air purification system may discolor over time as a result of chemical adsorption; therefore, one manner of monitoring the remaining efficiency of the adsorbent media is to check its discoloration or level of chemical activity. Another method of analyzing the existing lifetime of an adsorbent media bed is with a monitoring rod that changes color as more of the chemical is passed through the system, which indicates the consumption of the media bed. However, both of these techniques are inexact which allows for a large margin of error in determining the proper time for changing out the media of a system. These techniques also require the operator of the air purification system to physically go out and check them, which can be both arduous and highly inconvenient. Therefore there is an unmet need in the industry to address the abovementioned deficiencies.

SUMMARY OF THE INVENTION

Embodiments of the present invention provide a media bed monitoring device and system. Briefly described, the present invention is directed to a method for manufacturing a device for electronically monitoring the consumption of gas adsorbent media in a media bed includes forming a monitoring rod of a corrosion resistant material. A plurality of sensors are attached to an exterior surface of the monitoring rod, and a communication channel is routed between each sensor and the connecting rod.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIG. 2A is a schematic diagram of a detail of the media bed monitoring rod of FIG. 1 illustrating the wiring used in the monitoring rod shown.

FIG. 2B is a schematic diagram of a cutaway detail of the media bed monitoring rod of FIG. 1 illustrating a sensor deployed in the monitoring rod.

DETAILED DESCRIPTION

Figure 1:
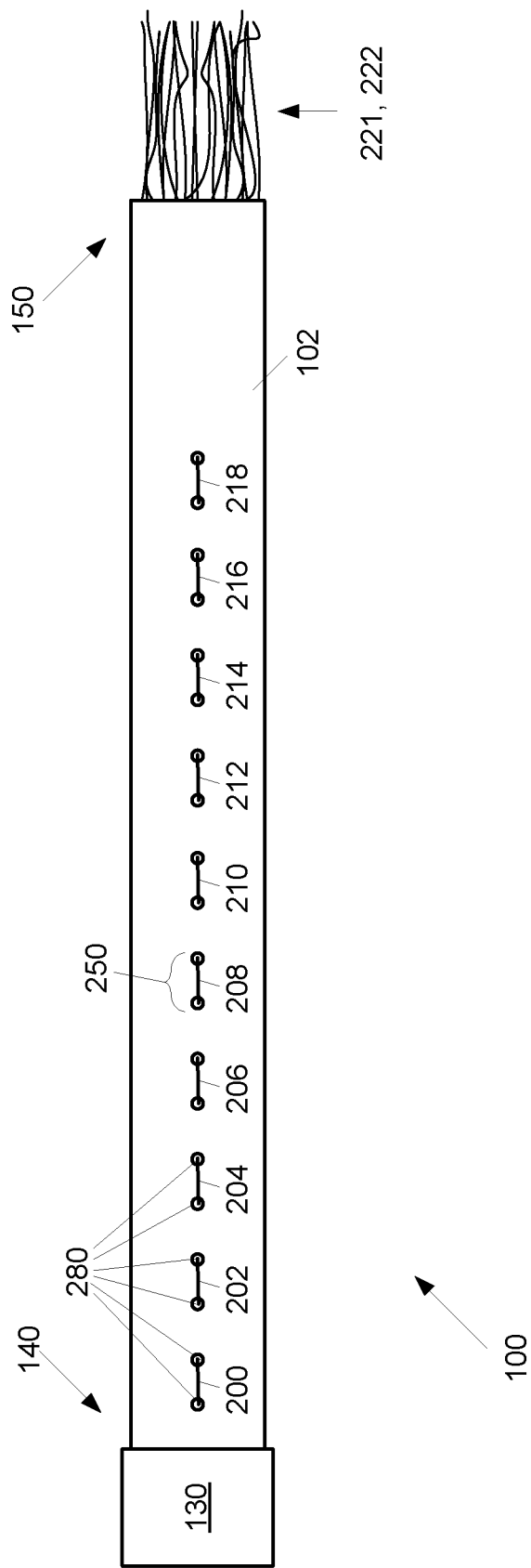
FIG. 1 is a schematic diagram of the front of an exemplary embodiment of a media bed monitoring rod.

Reference will now be made in detail to embodiments of the present invention, examples of which are illustrated in the accompanying drawings. Wherever possible, the same reference numbers are used in the drawings and the description to refer to the same or like parts.

In general, embodiments of media bed monitoring rods include a plurality of sensors mounted on the rod. The sensors are made from corrodible materials. Corrosion of the sensors is electronically monitored, where the rate of corrosion is used to estimate the remaining useful life of the adsorbent media bed.

Figure 3:
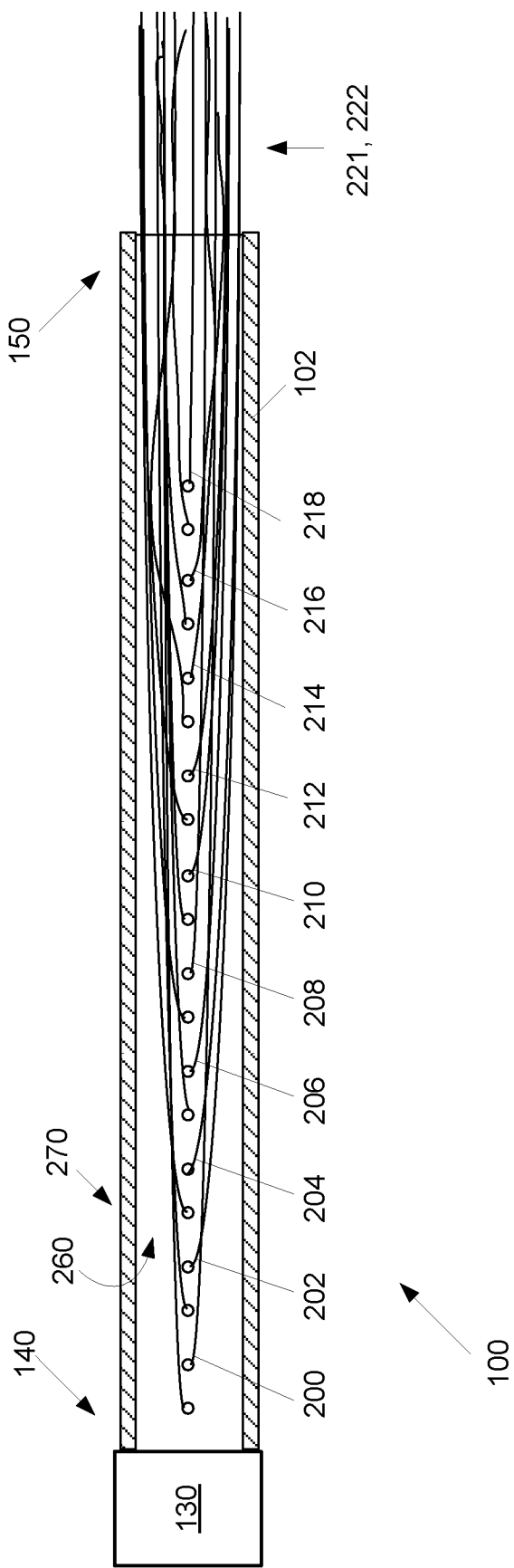
FIG. 3 is a schematic diagram of a cross-sectional view of the media bed monitoring rod portion of the media bed monitoring system.

Under a first embodiment of a media bed monitoring rod, a plurality of sensors may be implemented as shielded wires, where each of the shielded wires includes an exposed, unshielded portion, which will be referred to herein as a corrodible portion. FIGS. 1, 2A, 2B, and 3 depict aspects of the first embodiment of a media bed monitoring rod 100. FIG. 1 shows the monitoring rod 100 with a plurality of exposed wire sensors 200, 202, 204, 206, 208, 210, 212, 214, 216, 218. The wire sensors 200, 202, 204, 206, 208, 210, 212, 214, 216, 218 include a first lead 221 and a second lead 222 attached to, and electrically in contact with, the corrodible portion 250. The wire sensors 200, 202, 204, 206, 208, 210, 212, 214, 216, 218 indicate a resistance and/or permittivity change when the corrodible portion 250 is subjected to one or more corrosive agents. Alternatively, the wire sensors 200, 202, 204, 206, 208, 210, 212, 214, 216, 218 may be monitored for electrical continuity, rather than resistance and/or permittivity changes. FIG. 2A shows a detail of one of the wire sensors 200, 202, 204, 206, 208, 210, 212, 214, 216, 218 used in the monitoring rod 100 shown in greater detail. FIG. 3 shows a segment of a cross-sectional view of the present media bed monitoring rod 100 depicting the wiring within an interior 260 of the rod 100, where the corrodible portion 250 of the wire sensors 200, 202, 204, 206, 208, 210, 212, 214, 216, 218 may be disposed along an exterior portion 270 of the rod 100, where the corrodible portions 250 may be better exposed to the corrosive agent(s). The electrical leads 221, 222 may extend through the proximal end 150 of the tube 102.

The wire sensors 200, 202, 204, 206, 208, 210, 212, 214, 216, 218 may include a wire core made of one or more metals which can corrode, for example silver or copper or steel, among other metals, and may be completely shielded and/or clad except for a small segment of the wire (the corrodible portion 250) that is exposed to allow corrosion as shown in FIG. 2A. Under the first embodiment, the wire shielding for the wire sensors 200, 202, 204, 206, 208, 210, 212, 214, 216, 218 generally encloses the electrical leads 221, 222, and may include an insulated conductor, or the electrical leads 221, 222 may merely be protected from the corrosive agent(s) by a covering or cladding, for example, rubber or plastic cladding.

FIG. 2B is a schematic diagram of a cutaway detail of the media bed monitoring rod 100 illustrating a sensor 200 deployed in the monitoring rod 100. The sensor electrical leads 221, 222 are threaded through apertures (holes) 280 in the rod 100, such that the corrodible portion 250 is at least partially disposed on the exterior 270 of the rod 100, while the electrical leads 221, 222 are generally disposed within the rod interior. The apertures 280 may optionally be sealed with a corrosion resistant sealing material 290. In alternative embodiments, the wire sensors 200, 202, 204, 206, 208, 210, 212, 214, 216, 218 may be formed of an uninsulated wire, where a portion of the wire is exposed to corrodible materials on the rod 100 exterior 270, while the remaining portions of the wire are disposed within the rod 100 interior 260, for example via rod apertures between the exterior 270 and interior 260.

The sensors 200, 202, 204, 206, 208, 210, 212, 214, 216, 218 may incorporate any technology which reads the concentration of a targeted gas. The monitoring rod 100 includes a tube 102 formed of corrosion resistant tubing material. The tube 102 houses the corrosion susceptible wire sensors 200, 202, 204, 206, 208, 210, 212, 214, 216, and 218. The tube 102 may be substantially hollow, with apertures 280 between the interior 260 and exterior 270 to route the wire sensors 200, 202, 204, 206, 208, 210, 212, 214, 216, 218 between the interior 260 and exterior 270 of the tube 102. The tube 102 includes a distal end 140 and a proximal end 150, where the distal end 140 may be a closed end, and the proximal end 150 may be an open end. The distal end 140 of the tube 102 may be closed with an end cap 130 formed of the same or a different corrosion resistant material as the corrosion resistant tube 102, for example, to prevent intrusion of corrosive agents into the interior 260 of the rod 100.

The wire sensors 200, 202, 204, 206, 208, 210, 212, 214, 216, 218 may be equally spaced apart on the side of the tube 102 in a manner that allows for the exposed segment of each wire, the corrodible portion 250, to lie upon the exterior 270 of the tube 102 as shown in FIG. 1. For example, the non-exposed portion of the wires (leads 221, 222) may be woven into apertures 280 in the side of the tube 102, such that only the exposed portions of the wires (corrodible portion 250) are visible on the exterior of the tube 102. In addition, the ends 221, 222 of each of the wire sensors 200, 202, 204, 206, 208, 210, 212, 214, 216, 218 may protrude out of an opening in the proximal end 150 of the tube 102 as can be shown in FIG. 3, where the end opening is substantially on the opposite end of the tube 102 as the end cap 130. The apertures in the tube 102 may be sealed with a sealing material 290, epoxy, urethane, and/or silicone for example, around the wire sensors 200, 202, 204, 206, 208, 210, 212, 214, 216, 218 to prevent intrusion of the corroding agents into the interior 260 of the rod 100. The interior 260 of the tube 102 may similarly be filled with a sealing or potting material (not shown), epoxy, urethane, and/or silicone for example, to secure and maintain the wire sensors 200, 202, 204, 206, 208, 210, 212, 214, 216, 218 within the tube 102.

Figure 5:
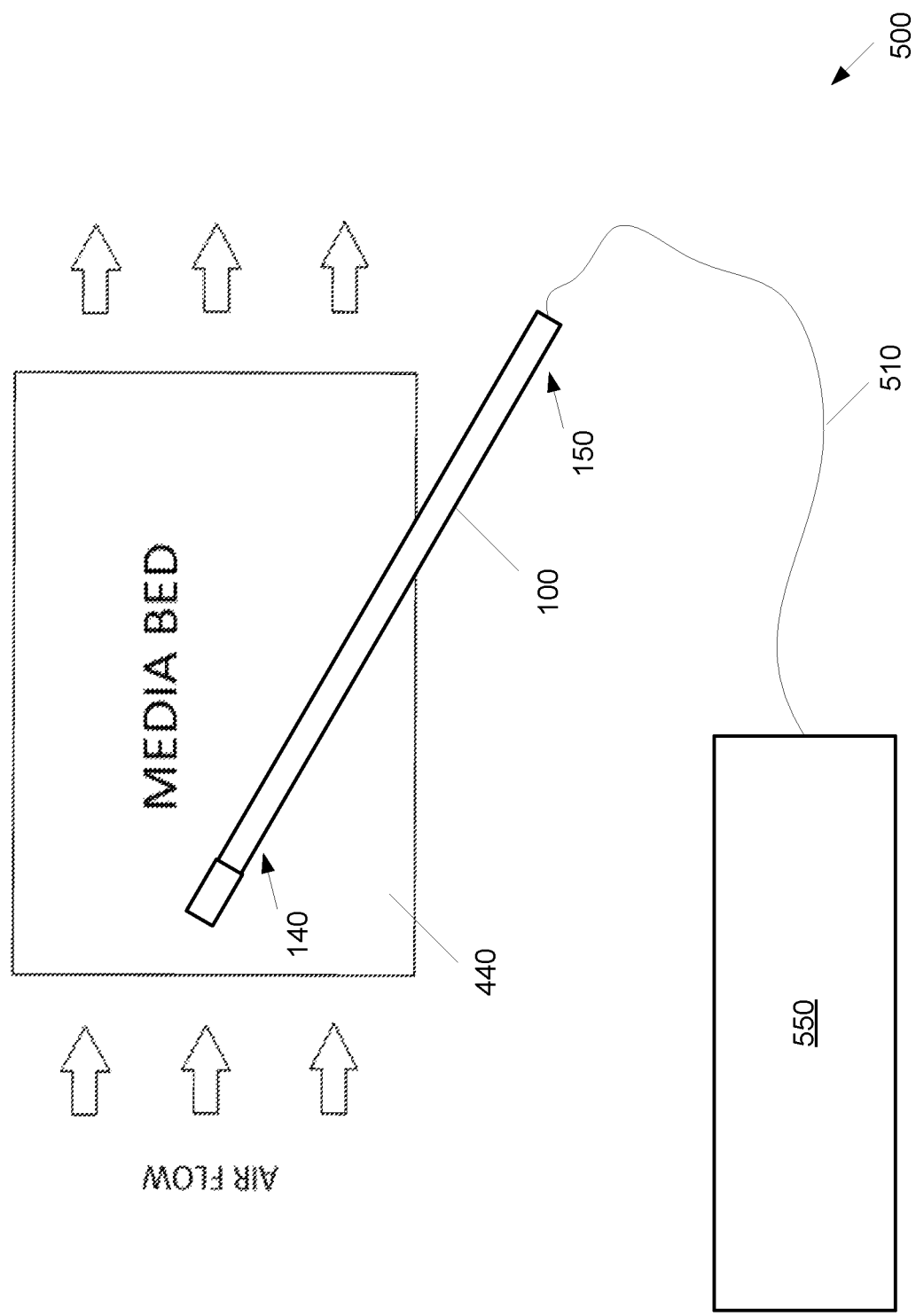
FIG. 5 is a schematic diagram of the exemplary embodiment of a media bed monitoring system.

Both ends of each of the wire sensors 200, 202, 204, 206, 208, 210, 212, 214, 216, 218, namely electrical leads 221, 222, may be connected to a controller, for example, a programmable logic controller (PLC) 550 (FIG. 5). The connection of the wire sensors 200, 202, 204, 206, 208, 210, 212, 214, 216, 218 to the PLC 550 (FIG. 5) may be direct via hard wiring, indirect, for example via additional circuit components (not shown), or via an intervening connecting device, which may be wired or wireless. Additional circuit components may be, for example, but not limited to, filtering components, buffering components, amplifiers, repeaters, analog-to-digital converters, among other components.

While the first embodiment of the monitoring rod 100 includes ten wire sensors 200, 202, 204, 206, 208, 210, 212, 214, 216, 218, there is no objection to embodiments where the monitoring rod 100 has fewer than ten sensors, or embodiments where the monitoring rod 100 has more than ten sensors.

While the first embodiment as shown by FIG. 1 depicts the exposed corrodible portions 250 of the wire sensors 200, 202, 204, 206, 208, 210, 212, 214, 216, 218 running in a lengthwise direction corresponding to a long axis of the rod 100, there is no objection to embodiments where the sensors are oriented differently, for example, in a diagonal orientation, or wrapping radially around a portion or all of the rod 100. Similarly, while the rod 100 is depicted as being substantially cylindrical in shape, in alternative embodiments the rod 100 may have other shapes, for example, a rectangular, oval, or other shaped cross section profile.

In an alternative embodiment, instead of routing all but the unshielded portion of the wires through the interior of the tube 102, the wires may be configured to run along the exterior of the tube 102, such that the each wire is shielded except for a short, unshielded corrodible portion 250, such that for each sensor the corrodible portion 250 is positioned at a different location along the length of the tube 102. In such an alternative embodiment, the rod 100 may not be hollow, but rather solid with all sensors and leads running on the surface of the rod 100. Alternatively, the corrodible portions 250 may be on the exterior of the rod 100, but some or all of the sensor leads may be partially or entirely embedded within a solid core of the rod 100.

Figure 4:
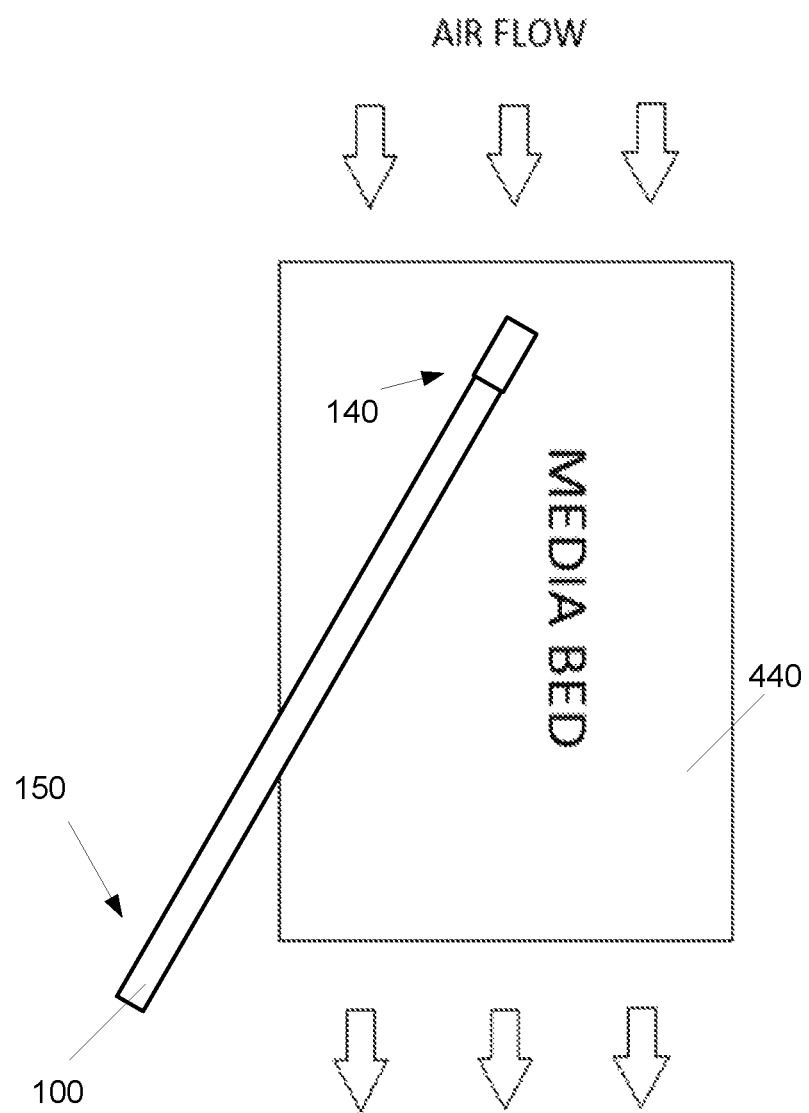
FIG. 4 is a schematic diagram of a media bed monitoring system installed in a bed of media.

FIG. 4 is a line diagram depicting the media bed monitoring rod 100 installed in a bed 440 of adsorbent media. The media bed monitoring rod 100 may be inserted into the media bed 440 at such an angle that the wire sensors 200, 202, 204, 206, 208, 210, 212, 214, 216, 218 are able to provide measurement across the media bed 440 in the direction of airflow. Alternatively, the rod 100 may be mounted parallel with the airflow. The adsorbent media bed 440 may include, for example, activated carbon, activated carbon with additives, alumina, impregnated alumina, zeolite, impregnated zeolite, or other adsorbents used to capture gases. The media bed monitoring rod 100 is place into the media bed 440 with the open end of the tube 102 (FIG. 1), proximal end 150, extending out of media and the closed end of the tube 102 (FIG. 1), distal end 140, oriented against the direction of airflow through the media bed 440 as shown in FIG. 4. The PLC 550 (FIG. 5) may then be mounted outside of the media bed 440 to the air purification system. In alternative embodiments, the PLC 550 (FIG. 5) may be integrated into the monitoring rod 100, for example at the proximal end 150 of the tube 102 (FIG. 1).

As a result of the media bed monitoring rod 100 being located in the media bed 440, the exposed wire sensors 200, 202, 204, 206, 208, 210, 212, 214, 216, 218 (FIG. 1) may be subjected to the substantially the same amount of chemicals as the adsorbent media in the media bed 440 is while the air purification system is operating. The adsorbent media in the media bed 440 progressively becomes depleted due to gases passing through the media bed 440. As a result, the corrodible portions 250 of the wire sensors 200, 202, 204, 206, 208, 210, 212, 214, 216, 218 (FIG. 1) progressively become exposed to more chemicals in their respective order at substantially the same rate the media is being exhausted. This exposure to chemicals causes corrosion of the wire sensors 200, 202, 204, 206, 208, 210, 212, 214, 216, 218 (FIG. 1) that are spaced apart on the media bed monitoring rod 100.

Due to this corrosion, certain electrical properties of the exposed wire sensors 200, 202, 204, 206, 208, 210, 212, 214, 216, 218 (FIG. 1), such as resistance, conductance, and/or continuity, may change. The PLC 550 (FIG. 5) measures these electrical characteristics and detects the changes occurring as more chemicals filter through the media bed 440. As programmed, the PLC 550 (FIG. 5) tracks the change of the electrical properties of the wire sensors 200, 202, 204, 206, 208, 210, 212, 214, 216, 218 (FIG. 1) and calculates the amount of chemicals that have gone through the air purification system. Arising from this, the PLC 550 (FIG. 5) is able to monitor the adequacy of the adsorbent media in the media bed 440. For example, the rod 100 may be located in the media bed 440 such that each of the wire sensors 200, 202, 204, 206, 208, 210, 212, 214, 216, 218 is positioned at a different depth within the media in the media bed 440. Differing corrosion levels of the wire sensors 200, 202, 204, 206, 208, 210, 212, 214, 216, 218 (FIG. 1) may occur according to the depth of the corresponding wire sensors 200, 202, 204, 206, 208, 210, 212, 214, 216, 218 (FIG. 1) within the adsorbent media.

In alternative embodiments, rather than partially shielded wires, the sensors may be implemented by other means, for example, with a corrodible portion implemented as flat or curved metallic pads, metal traces deposited on the exterior of the rod 100, or other means familiar to persons having ordinary skill in the art. In each of these embodiments, the electrical permittivity/resistivity/continuity through the sensors is affected by corrosion from exposure to gasses flowing through the media bed. Two or more sensors may be co-located adjacent to one another, where the co-located sensors are configured to detect different characteristics of the adsorbing media. For example, a first co-located sensor may be formed of a first material more sensitive to corrosion from a first corrosive agent, while a second co-located sensor may be formed of a second material more sensitive to corrosion from a second corrosive agent. In this way, the rod 100 may be configured to detect distinct corrosion patterns due to two or more corrosive agents.

FIG. 5 shows an exemplary embodiment of a monitoring system 500 including a monitoring rod 100 and a PLC 550. The monitoring rod 100 may be located in the monitoring bed 440 of an air purification device. The monitoring bed 440 includes an adsorbent media. The monitoring rod 100 is connected to the PLC 550 via a connection 510. As described above, the connection 510 may be a wired connection including one or more electrically conducting wires, for example, copper wires, or may be a wireless connection, for example, using Wi-Fi, Bluetooth, ZigBee, or other wired or wireless communication protocols. The connection 510 allows the PLC 550 to monitor the corrosion levels of wire sensors 200, 202, 204, 206, 208, 210, 212, 214, 216, 218 (FIG. 1).

The PLC 550 includes circuitry, for example, relays and measurement devices, to detect a change in the sensor wires sensors 200, 202, 204, 206, 208, 210, 212, 214, 216, 218 (FIG. 1). The PLC 550 may measure the resistance and/or permittivity and/or continuity of each of the sensor wires sensors 200, 202, 204, 206, 208, 210, 212, 214, 216, 218 (FIG. 1), for example, by inducing an electric current through each of the sensor wires sensors 200, 202, 204, 206, 208, 210, 212, 214, 216, 218 (FIG. 1). The PLC 550 utilizes one or more processes, for example, software processes, which translate the activity detected by the wire sensors 200, 202, 204, 206, 208, 210, 212, 214, 216, 218 (FIG. 1) into adsorbent media consumption and projected adsorbent media expiration.

The PLC 550 may include communications options to provide information through available wired or wireless analog and/or digital communications. The PLC may provide an indication that the adsorbent media has expired, or that the adsorbent media is predicted to expire within a given period of time, for example, in a matter of hours, days, or weeks. Such an indication may be, for example but not limited to, by a visual indicator, such as illuminating or flashing a lamp, an audio indicator, for example, an audible tone or buzzer, or by transmitting a message, for example, a text message or email message via a communication network.

Due to the ability of the media bed monitoring rod 100 in accordance with the PLC 550, an operator of the adsorbent system can effectively monitor the remaining lifetime of the media with a precision and predictability that other methods lack. The PLC 550 also can project when the media needs changing based on the data collected from the media bed monitoring rod and alert the operator of the system of the date it has determined. This serves to ensure that the adsorbent media is replaced in a timely manner and not neglected to keep the air purification system effective while also providing a convenient way for the operator to maintain the air purification system.

Figure 6:
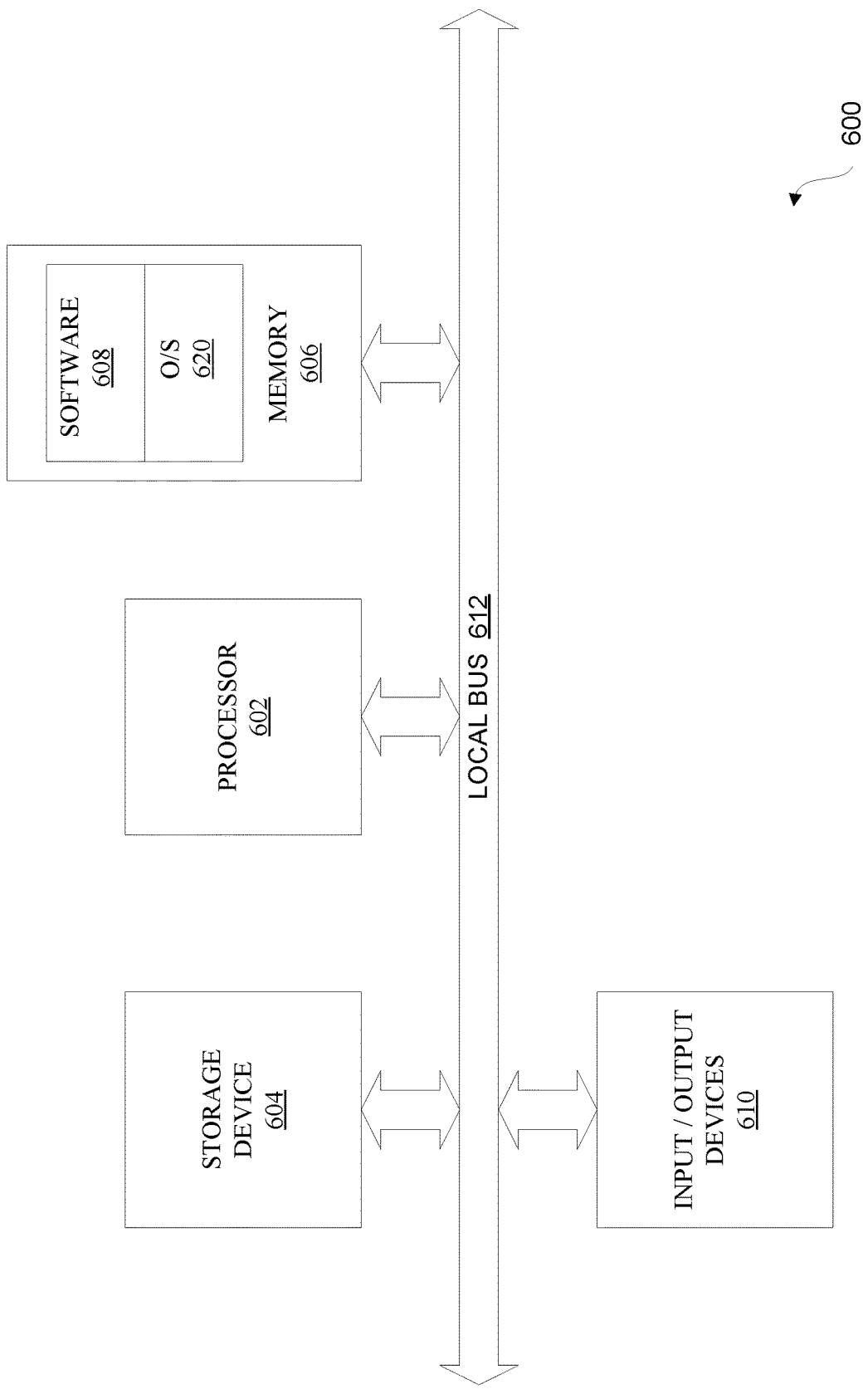
FIG. 6 is a schematic diagram illustrating an example of a system for executing functionality of the programmable logic controller.

The present system 600 for executing the functionality of the PLC 550 described in detail above may be a computer, an example of which is shown in the schematic diagram of FIG. 6. The system 600 contains a processor 602, a storage device 604, a memory 606 having software 608 stored therein that defines the abovementioned functionality, input and output (I/O) devices 610 (or peripherals), and a local bus, or local interface 612 allowing for communication within the system 600. The local interface 612 can be, for example but not limited to, one or more buses or other wired or wireless connections, as is known in the art. The local interface 612 may have additional elements, which are omitted for simplicity, such as controllers, buffers (caches), drivers, repeaters, and receivers, to enable communications. Further, the local interface 612 may include address, control, and/or data connections to enable appropriate communications among the aforementioned components.

The processor 602 is a hardware device for executing software, particularly non transient instructions that are stored in the memory 606. The processor 602 can be any custom made or commercially available single core or multi-core processor, a central processing unit (CPU), an auxiliary processor among several processors associated with the present system 600, a semiconductor based microprocessor (in the form of a microchip or chip set), a macroprocessor, or generally any device for executing software instructions.

The memory 606 can include any one or combination of volatile memory elements (e.g., random access memory (RAM, such as DRAM, SRAM, SDRAM, flash memory, thumb drives, etc.)) and nonvolatile memory elements (e.g., ROM, hard drive, tape, CDROM, etc.). Moreover, the memory 606 may incorporate electronic, magnetic, optical, and/or other types of storage media. Note that the memory 606 can have a distributed architecture, where various components are situated remotely from one another, but can be accessed by the processor 602.

The software 608 defines functionality performed by the system 600, in accordance with the present invention. The software 608 in the memory 606 may include one or more separate programs, each of which contains an ordered listing of executable instructions for implementing logical functions of the system 600, as described below. The memory 606 may contain an operating system (O/S) 620. The operating system essentially controls the execution of programs within the system 600 and provides scheduling, input-output control, file and data management, memory management, and communication control and related services.

The I/O devices 610 may include input devices, for example but not limited to, the wire sensors 200, 202, 204, 206, 208, 210, 212, 214, 216, 218 (FIG. 1), as well as control devices, such as a keyboard, mouse, scanner, microphone, etc. Furthermore, the I/O devices 610 may also include output devices, for example but not limited to, a printer, display, etc. Finally, the I/O devices 610 may further include devices that communicate via both inputs and outputs, for instance but not limited to, a modulator and/or demodulator (for accessing and/or providing access to another device, system, or network), a radio frequency (RF) or other wireless transceiver, a telephonic interface, a bridge, a router, or other device.

When the system 600 is in operation, the processor 602 is configured to execute the software 608 stored on non-transitory media within the memory 606, to communicate data to and from the memory 606, and to generally control operations of the system 600 pursuant to the software 608, as explained above.

Figure 7:
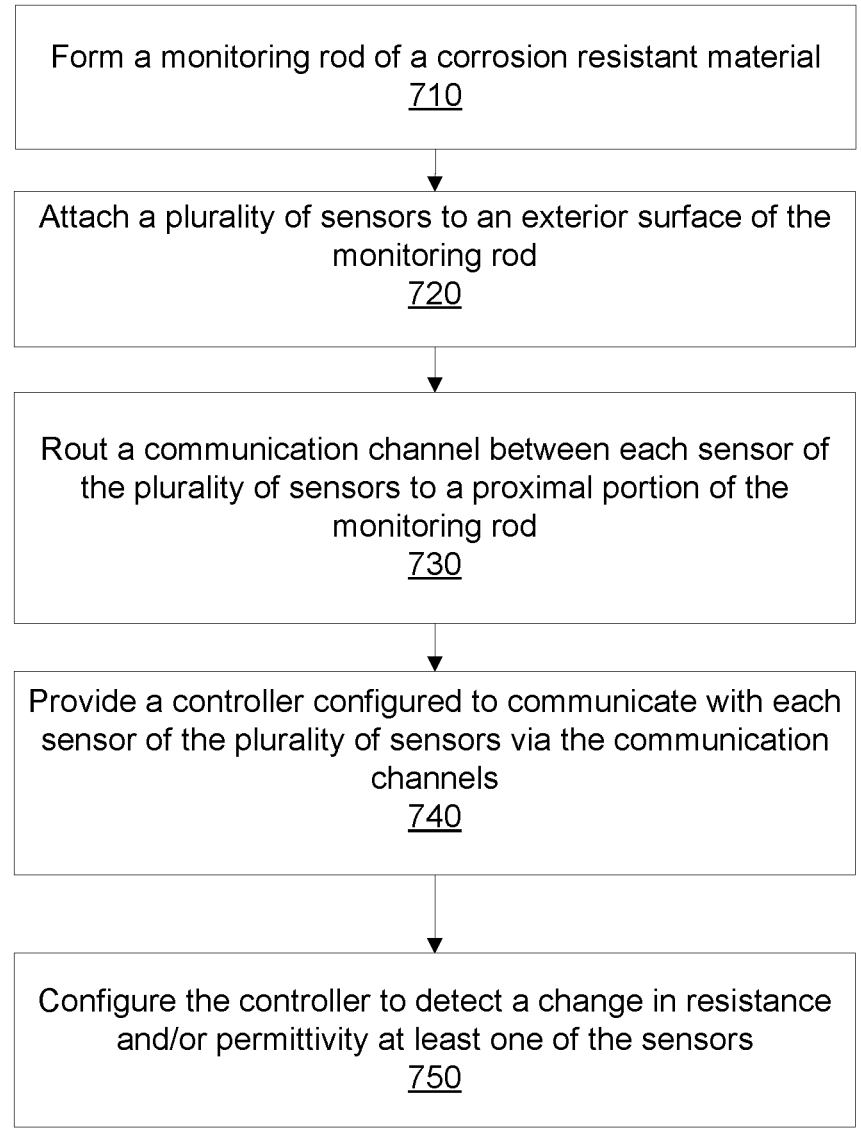
FIG. 7 is a flowchart of an exemplary method for manufacturing a device for electronically monitoring the consumption of gas adsorbent media in a media bed.

FIG. 7 is a flowchart 700 of an exemplary method for manufacturing a device for electronically monitoring the consumption of gas adsorbent media in a media bed. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

A monitoring rod 100 (FIG. 1) is formed of a corrosion resistant material, as shown by block 710. A plurality of sensors 200 (FIG. 1) is attached to an exterior surface of the monitoring rod, as shown by block 720. The sensors 200 (FIG. 1) may include a corrodible portion 250 (FIG. 1) having an exposed electrically conducting material susceptible to corrosion by a corrosive agent. A communication channel is routed between each sensor 200 (FIG. 1) of the plurality of sensors to a proximal portion 150 (FIG. 1) of the monitoring rod 100 (FIG. 1), as shown by block 730. A controller 550 (FIG. 5) is configured to communicate with each sensor 200 (FIG. 1) of the plurality of sensors via the communication channels, as shown by block 740. The controller 550 (FIG. 5) is configured to detect a change in resistance and/or permittivity at least one of the sensors 200 (FIG. 1), as shown by block 750

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

I claim:

1. A sensor rod in communication with a controller, comprising:
   a plurality of wire sensors configured on a rod, each of the plurality of wire sensors comprising an unshielded wire portion corrodible by one or more corrosive materials when the rod is exposed to an environment comprising the one or more corrosive materials,
   wherein each of the plurality of wire sensors is in communication with a controller configured to measure changes in one or more electrical characteristics of each of the plurality of wire sensors, and wherein the changes in the one or more electrical characteristics of each of the plurality of wire sensors is detectable by the controller when each of the corrodible unshielded wire portions is exposed to the one or more corrosive materials in the environment.

2. The sensor rod of claim 1, wherein the one or more corrosive materials comprises a gas that is targeted for monitoring in the environment.

3. The sensor rod of claim 1, wherein:
   the rod comprises a plurality of apertures;
   each of the plurality of wire sensors is threaded through an aperture in the plurality of apertures;
   the corrodible unshielded wire portion of each of the plurality of wire sensors is at least partially disposed on an exterior of the rod;
   an interior wire sensor portion of each of the plurality of wire sensors is disposed on an interior of the rod; and
   each of the interior wire sensor portions has a first end portion configured with a first lead and a second end portion configured with a second lead to provide a continuous electrical circuit from each of the plurality of wire sensors to the controller.

4. The sensor rod of claim 3, wherein the rod is configured to prevent intrusion of the one or more corrosive materials into the rod interior.

5. The sensor rod of claim 3, wherein a change in resistance or permittivity of the continuous electrical circuit of one or more of the plurality of wire sensors indicates when the corrodible unshielded wire portion is exposed to the one or more corrosive materials.

6. The sensor rod of claim 1, wherein a first sensor comprises a first material that is corrodible from exposure to a first corrosive material and a second sensor comprises a second material that is corrodible from exposure to a second corrosive material to allow at least two corrosive materials present in the environment to be targeted for monitoring.

7. The sensor rod of claim 6, wherein each of the first and second corrosive materials comprises a gas.

8. The sensor rod of claim 1, wherein the rod is configurable to monitor an amount of the one or more corrosive materials filtered through an absorbent media bed in which the device has been installed.

9. A system for monitoring one or more corrosive materials in an environment, comprising:
- a monitoring rod comprising a plurality of wire sensors configured on the monitoring rod, wherein:
    - an unshielded wire portion of each of the plurality of wire sensors is corrodible by one or more corrosive materials when the corrodible unshielded wire portion is exposed to an environment comprising the one or more corrosive materials; and
    - each of the plurality of wire sensors is in communication with a controller comprising a memory and logic configured to execute non-transient instructions, to measure one or more electrical characteristics of each of the plurality of wire sensors, and to detect changes in the one or more electrical characteristics of one or more of the plurality of wire sensors when at least some of the corrodible unshielded wire portion of each of the plurality of wire sensors is exposed to the one or more corrosive materials in the environment.

10. The system of claim 9, wherein:
the plurality of wire sensors are threaded through apertures in the monitoring rod to at least partially dispose the corrodible unshielded wire portion of the plurality of wire sensors on an exterior of the monitoring rod;
at least an interior wire sensor portion of each of the plurality of wire sensors is disposed on an interior of the monitoring rod; and
each of the interior wire sensor portions has a first end portion configured with a first lead and a second end portion configured with a second lead to provide a continuous electrical circuit from each of the plurality of wire sensors to the controller.

11. The system of claim 10, wherein the monitoring rod is configured to prevent intrusion of the one or more corrosive materials into the interior of the monitoring rod.

12. The system of claim 10, wherein the continuous electrical circuit indicates a change in resistance or permittivity in that wire sensor.

13. The system of claim 9, wherein the controller is configured to monitor an amount of the one or more corrosive materials filtered through an absorbent media bed in which the monitoring rod has been incorporated.

14. An air monitoring system, comprising:
- a gas absorbent media bed; and
- a monitoring rod comprising a plurality of wire sensors configured on the monitoring rod, wherein:
    - a portion of each of the plurality of wire sensors is corrodible by one or more corrosive materials in an environment comprising the one or more corrosive materials;
    - the corrodible portion of each of the plurality of wire sensors comprises an unshielded wire portion exposable to the environment; and
    - each of the plurality of wire sensors is in communication with a controller configured to measure one or more electrical characteristics of each of the plurality of wire sensors and to detect changes in the one or more electrical characteristics of the plurality of wire sensors when at least some of the corrodible portion of at least one of the plurality of wire sensors is exposed to the one or more corrosive materials in the environment.

15. The air monitoring system of claim 14, configured to determine an amount of the one or more corrosive materials passing through the gas absorbent media bed.

16. The air monitoring system of claim 14, wherein the one or more corrosive materials comprises a gas.

17. The air monitoring system of claim 14 wherein the controller is configured to generate an alert to an operator to replace the gas absorbent media bed.

18. The air monitoring system of claim 14, wherein the monitoring rod is disposed within the gas adsorbent media bed at an angle configured so the plurality of wire sensors provide a measurement of the one or more corrosive material in the environment across the gas adsorbent media bed in a direction of airflow.

19. The air monitoring system of claim 14, wherein the monitoring rod is disposed within the gas adsorbent media bed parallel with a direction of airflow.

20. The air monitoring system of claim 14, wherein the controller is mounted outside of the gas adsorbent media bed or is integrated into the monitoring rod.

* * * * *